United States Patent
Tao et al.

(10) Patent No.: US 12,029,501 B2
(45) Date of Patent: Jul. 9, 2024

(54) AUTOMATED INSTRUMENT-TRACKING AND ADAPTIVE IMAGE SAMPLING

(71) Applicant: Vanderbilt University, Nashville, TN (US)

(72) Inventors: Yuankai Tao, Nashville, TN (US); Mohamed T. El-Haddad, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 252 days.

(21) Appl. No.: 17/421,558

(22) PCT Filed: Jan. 10, 2020

(86) PCT No.: PCT/US2020/013137
§ 371 (c)(1),
(2) Date: Jul. 8, 2021

(87) PCT Pub. No.: WO2020/146764
PCT Pub. Date: Jul. 16, 2020

(65) Prior Publication Data
US 2022/0061929 A1    Mar. 3, 2022

Related U.S. Application Data

(60) Provisional application No. 62/791,350, filed on Jan. 11, 2019.

(51) Int. Cl.
*A61B 34/20*    (2016.01)
*A61B 90/00*    (2016.01)
(Continued)

(52) U.S. Cl.
CPC .......... *A61B 34/20* (2016.02); *G01B 9/02091* (2013.01); *G06T 3/40* (2013.01);
(Continued)

(58) Field of Classification Search
CPC ............ A61B 34/20; A61B 2034/2065; A61B 2034/2055; A61B 2090/373;
(Continued)

(56) References Cited

U.S. PATENT DOCUMENTS

| 2005/0035295 A1 | 2/2005 | Buoma et al. |
| 2008/0100612 A1 | 5/2008 | Dastmalchi et al. |

(Continued)

OTHER PUBLICATIONS

Anwar, S.M., Majid, M., Qayyum, A. et al. Medical Image Analysis using Convolutional Neural Networks: A Review. J Med Syst 42, 226 (2018). https://doi.org/10.1007/s10916-018-1088-1 (Year: 2018).*

(Continued)

*Primary Examiner* — Uzma Alam
*Assistant Examiner* — Jonathon Cook
(74) *Attorney, Agent, or Firm* — Michael Best & Friedrich LLP

(57) ABSTRACT

Systems and methods for image-based guidance using automated instrument tracking. An en face image frame, generated from en face image data captured by a first imaging system (e.g., an SER imaging system), is analyzed to determine a location of an instrument in the first imaging plane. A control signal is then generated for the movement stage to control the scanning movement of a depth-based imaging system (e.g., an OCT imaging system) based on the determined location of the instrument. In some implementations, a trained neural-network is used to determine the location of the instrument based on the en face image frame and, in some implementations, the control signal adjusts the speed of the scanning movement to capture image data at a higher density7 at areas corresponding to the determined location of the instrument.

15 Claims, 6 Drawing Sheets

(51) Int. Cl.
 G01B 9/02091 (2022.01)
 G06T 3/40 (2024.01)
 G06T 7/70 (2017.01)
(52) U.S. Cl.
 CPC ........ *G06T 7/70* (2017.01); *A61B 2034/2065* (2016.02); *A61B 2090/373* (2016.02); *G06T 2207/10028* (2013.01); *G06T 2207/10101* (2013.01); *G06T 2207/20084* (2013.01)
(58) Field of Classification Search
 CPC .............. A61B 2090/3735; G06T 7/70; G06T 2207/10101; G06T 2207/20084; G01B 9/02091
 See application file for complete search history.

(56) References Cited

U.S. PATENT DOCUMENTS

| | | | |
|---|---|---|---|
| 2009/0021724 A1 | 1/2009 | Mahadevan-Jansen et al. | |
| 2011/0043661 A1 | 2/2011 | Podoleanu | |
| 2012/0184846 A1* | 7/2012 | Izatt | A61B 3/132 356/479 |
| 2013/0120757 A1 | 5/2013 | Yu et al. | |
| 2014/0221822 A1* | 8/2014 | Ehlers | A61B 5/061 600/424 |
| 2015/0157205 A1 | 6/2015 | Buckland et al. | |
| 2016/0324593 A1 | 11/2016 | El-Haddad et al. | |
| 2019/0110682 A1* | 4/2019 | Charles | A61B 3/12 |

OTHER PUBLICATIONS

Carrasco-Zevallos et al., "Review of intraoperative optical coherence tomography: technology and applications", Biomed Opt. Express, vol. 8, No. 3, 2017, pp. 1607-1637.

Carrasco-Zevallos et al., "Live volumetric (4D) visualization and guidance of in vivo human ophthalmic surgery with intraoperative optical coherence tomography", Sci. Rep., vol. 6, No. 31689, 2016, 16 pages.

El-Haddad et al., "Automated stereo vision instrument tracking for intraoperative OCT guided anterior segment ophthalmic surgical maneuvers", Biomed. Opt. Express, vol. 6, No. 8, 2015, pp. 3014-3031.

El-Haddad et al., "Advances in intraoperative optical coherence tomography for surgical guidance", Curr. Opin. Biomed. Eng., vol. 3, 2017, pp. 37-48.

El-Haddad et al., "Spectrally encoded coherence tomography and reflectometry: Simultaneous en face and cross-sectional imaging at 2 gigapixels per second", J. Biophotonics, vol. 11, No. 4, 2018, p. e201700268, 10 pages.

El-Haddad et al., "Deep-learning based automated instrument tracking and adaptive-sampling of intraoperative OCT for video-rate volumetric imaging of ophthalmic surgical maneuvers", SPIE Proceedings, 2019, 7 pages.

Gessert et al., "A deep learning approach for pose estimation from volumetric OCT data", Med. Image Anal., vol. 46, 2018, pp. 162-179.

International Preliminary Report on Patentability for Application No. PCT/US20/13137 dated Jun. 16, 2021 (15 pages).

International Search Report and Written Opinion for Application No. PCT/US20/13137 dated Apr. 23, 2020 (15 pages).

Keller et al., "Real-time corneal segmentation and 3D needle tracking in intrasurgical OCT", Biomed. Opt. Express, vol. 9, No. 6, 2018, pp. 2716-2732.

Li et al., "Image-guided feedback for ophthalmic microsurgery using multimodal intraoperative swept-source spectrally encoded scanning laser ophthalmoscopy and optical coherence tomography", Proc. of SPIE vol. 2017, vol. 10053, 7 pages.

Malone et al., "Resolution and throughput optimized intraoperative spectrally encoded coherence tomography and reflectometry (iSECTR) for multimodal imaging during ophthalmic microsurgery", SPIE Proceedings, vol. 10483, 2018, 6 pages.

Redmon, "YOLOv3: An Incremental Improvement", ArXiv180402767 Cs, Apr. 2018, 6 pages . . . .

* cited by examiner

AUTOMATED INSTRUMENT-TRACKING AND ADAPTIVE IMAGE SAMPLING

RELATED APPLICATIONS

This patent application is the U.S. national stage entry, under 35 U.S.C. 371, of International Application Number PCT/US2020/013137, filed Jan. 10, 2020, which claims the benefit of U.S. Provisional Patent Application No. 62/791,350, filed Jan. 11, 2019, the entire contents of each of which are incorporated herein by reference.

STATEMENT REGARDING FEDERALLY SPONSORED RESEARCH

This invention was made with government support under grant numbers HL116597 and HL136449, awarded by the National Institutes of Health. The government has certain rights in the invention.

BACKGROUND

The present invention relates to imaging systems for intraoperative surgical guidance. In particular, some implementations relate to systems and methods for using optical coherence tomography (OCT) for image-based guidance during the performance of surgical procedures.

SUMMARY

Optical coherence tomography (OCT) is the current gold-standard for ophthalmic diagnostic imaging. Systems and methods, such as described herein, are proposed to demonstrate the utility of OCT for intraoperative guidance. However, one major limitation of intraoperative OCT is that imaging is limited to static fields-of-view (FOVs). This limitation is significant for the purposes of intraoperative guidance during surgical cases because surgical instruments move dynamically while performing surgical procedures.

In some implementations, the systems and methods described herein provide automated surgical instrument tracking using machine-learning. These technologies may be adapted and incorporated into new commercial products or provided as modular "add-ons" to existing surgical microscope systems. In some implementations, the system utilizes a machine-learning mechanisms trained to identify the position of one or more surgical instruments based on captured 2D image data and to use the identified position of the surgical instrument(s) to automatically adjust the field-of-view of OCT scanning. Additionally, in some implementations, adaptive sampling of the field-of-view is implemented so that image data is densely sampled at the point of interaction between the surgical instrument and the tissue relatively to the image sampling at other locations within the field-of-view of the imaging system (in which relatively sparse sampling is utilized).

In one embodiment, the invention provides an image-based guidance system comprising a first imaging system configured to capture enface image data in a first imaging plane, a second imaging system configured to capture depth image data in a second imaging plane orthogonal to the first imaging plane, and a movement stage configured to provide a scanning movement of the imaging systems. An en face image frame, generated from en face image data captured by the first imaging system, is analyzed to determine a location of an instrument in the first imaging plane. A control signal is then generated for the movement stage to control the scanning movement of the imaging systems based on the determined location of the instrument. In some implementations, a trained neural-network is used to determine the location of the instrument based on the en face image frame and, in some implementations, the control signal adjusts the speed of the scanning movement to capture image data at a higher density at areas corresponding to the determined location of the instrument.

In another embodiment, the invention provides a method for image-based guidance using automated instrument tracking. An en face image frame is received by an electronic controller. The en face image frame is generated based on en face image data captured by a first imaging system in a first imaging plane. The en face image frame is analyzed to determine a location of an instrument in the first imaging plane. In some implementations, the location of the instrument is determined from the en face image frame using a trained neural network. A control signal for a movement stage is then generated based on the determined location of the instrument. The movement stage is configured to provide a scanning movement of a second imaging system that is configured to capture depth image data in a second imaging plane during the scanning movement. In some implementations, the generated control signal is configured to slow the scanning movement when scanning in areas corresponding to the determined location of the instrument in order to provide an increased image sampling density in the areas corresponding to the determined location of the instrument.

In yet another embodiment, the invention provides an image-based guidance system including an OCT imaging system, a first galvanometer, a second galvanometer, and an en face imaging system (e.g., an SER imaging system). The first galvanometer is coupled to at least one imaging component of the OCT imaging system to provide scanning oscillations of the OCT imaging system in a first scanning direction and the second galvanometer is coupled to the at least one imaging component of the OCT imaging system to provide scanning oscillations of the OCT imaging system in a second scanning direction. The second scanning direction is orthogonal to the first scanning direction in a first imaging plane. The en face imaging system is configure to capture en face image data in the first imaging plane and is positionally co-registered with the OCT imaging system. At least one imaging component of the en face imaging system is coupled to the first galvanometer and the second galvanometer to provide scanning oscillations of the en face imaging system in the first scanning direction and the second scanning direction, respectively. An electronic controller is configured to apply a neural network that is configured to receive an en face image frame (based on image data received from the en face imaging system) as an input and to produce as output a bounding box defining a determined location of an instrument tip in the first imaging plane. A first control waveform for the first galvanometer and a second control waveform for the second galvanometer are generated based on the determined location of the instrument tip in the first scanning direction and the second scanning direction, respectively. The control waveforms are transmitted to the first galvanometer and the second galvanometer to control scanning movement of the OCT imaging system. OCT image data is captured by the OCT imaging system and received by the electronic controller while the scanning oscillations of the OCT imaging system are controlled based on the generated control waveforms.

Other aspects of the invention will become apparent by consideration of the details description and accompanying drawings.

DETAILED DESCRIPTION

Figure 1:
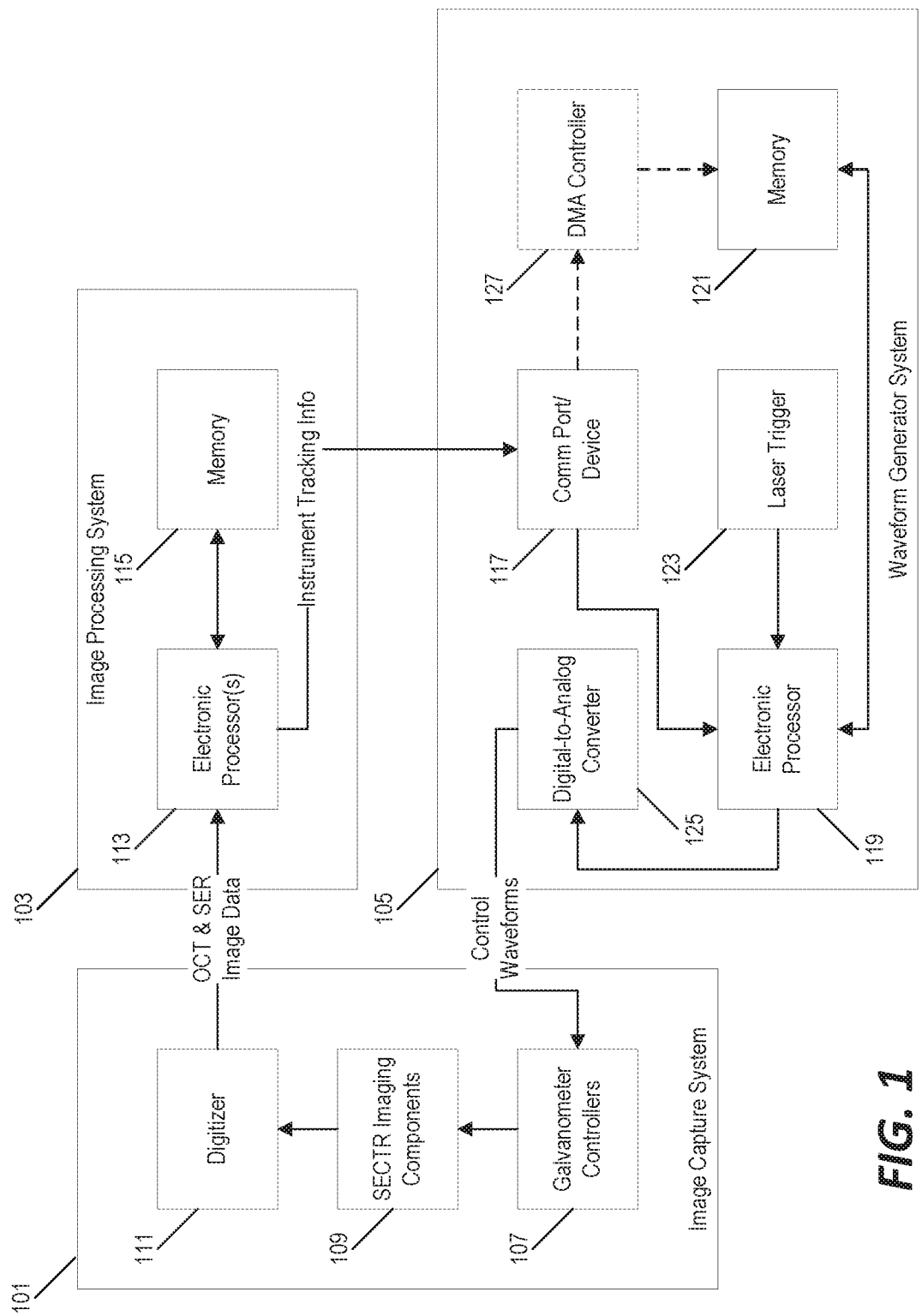
FIG. 1 is a block diagram of an OCT imaging system with automated instrument tracking and adaptive sampling according to one implementation.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

A plurality of hardware and software based devices, as well as a plurality of different structural components may be used to implement various embodiments. In addition, embodiments may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software (for example, stored on non-transitory computer-readable medium) executable by one or more processors. For example, "control units" and "controllers" described in the specification can include one or more electronic processors, one or more memory modules including non-transitory computer-readable medium, one or more input/output interfaces, one or more application specific integrated circuits (ASICs), and various connections (for example, a system bus) connecting the various components.

By the use of the techniques disclosed herein, one or more devices can be configured to conserve resources with respect to power resources, memory resources, communications bandwidth resources, processing resources, and/or other resources while providing mechanisms for enabling automated surgical instrument tracking. Technical effects other than those mentioned herein can also be realized from an implementation of the technologies disclosed herein.

Intraoperative optical coherence tomography (iOCT) enables volumetric imaging of surgical maneuvers, which can be used, for example, to verify completion of surgical goals. However, because the positioning of a surgical instrument will change dynamically while a surgical procedure is performed, techniques for adjusting the field-of-view to track a region-of-interest (e.g., the tip of the surgical instrument) may be needed in at least some implementations in order to utilize iOCT for real-time surgical feedback and iOCT-guided surgery. One option for automatically adjusting the field-of-view of the imaging system would be to utilize stereo-vision-based instrument tracking. However, accurate automatic instrument-tracking using stereo-vision may be limited to an anterior segment. Alternatively, volumetric OCT data might be used instrument tracking. However, although volumetric OCT methods allow for high-accurate tracking and pose estimation, the maximum tracking rate is limited by OCT acquisition speeds and a fundamental tradeoff between sampling density and field-of-view size.

FIG. 1 illustrates an example of an imaging system configured to utilize spectrally-encoded coherence tomography and reflectometry (SECTR) imaging for automated surgical instrument tracking and adaptive sampling of OCT that can be utilized, in some implementations, for real-time surgical feedback and iOCT-guided surgery. SECTR imaging provides simultaneous imaging of spatiotemporally co-registered orthogonal imaging plane—"en face" imaging provided by spectrally-encoded reflectometry (SER) image data and cross-sectional imaging provided by OCT image data. Using SECTR, the system of FIG. 1 is capable of capturing image data at rates of several gigapixels-per-second.

In the system of FIG. 1, a GPU-accelerated deep-learning neural-network is trained using SER images for detection and localization of a surgical instrument (e.g., a 25G internal limiting membrane (ILM) forceps) at up to 50 Hz. The trained neural network is then used to determine a location of the surgical instrument based on a captured 2D SER image. This positional information is then used for acquisition of adaptively sampled SER frames and OCT volume, which are densely-sampled at the instrument tip and sampled relatively-sparsely at other locations in the imaging field-of-view. The relative sparse sampling at areas other than the instrument tip reduce computational load while retaining image data that can be used to determine a location of the instrument tip when it is moved from its current location. This approach to automated instrument tracking provided by the system of FIG. 1 addresses barriers in the utility of iOCT for real-time surgical guidance by (1) reducing the instrument tracking problem to 2D space, which is simpler and more computationally efficient than 3D tracking or pose-estimation and (2) decoupling instrument tracking speed & performance from the performance limitations of the OCT system and its acquisition parameters.

The imaging system of FIG. 1 includes an image capture system 101, an image processing system 103, and a waveform generator system 105. The image capture system 101 includes two or more galvanometer controllers 107 configured to provide scanning oscillations for the imaging system in two directions by changing an angular position of at least one imaging component of the SECTR imaging components 109. For example, in some implementations, the SECTR imaging components 109 may include an arrangement of one or more lenses, mirrors, light sources, and imaging sensors configured to project light to a "spot" or "line" location and to capture image data reflected back to the one or more imaging sensor. The galvanometer controllers 107 may be configured to provide for "scanning" by oscillating one or more components of the SECTR imaging components 109 (e.g., a mirror or a lens) to move the spot or line location across the surface. By using the SECTR imaging platform, the SER image data and the OCT image data are inherently co-registered and, accordingly, locations of objects/structures in the SER image data can readily be located in the OCT image data by the image processing system 103.

Multiple galvanometer 107 controllers may be configured to operate in coordination to provide two-dimensional scanning and three-dimensional OCT imaging. For example, a first galvanometer controller 107 may be configured to oscillate back-and-forth in an x-direction while a second galvanometer controller 107 may be configured to oscillate in a y-direction. By controlling the galvanometer controllers 107 so that the oscillation speed of the second galvanometer controller is significantly slower than the oscillation speed of the first galvanometer controller, the system can be configured to perform multiple x-direction oscillations for each single y-direction oscillation. Each x-direction scan provides OCT imaging data for a single two-dimensional "slice" (i.e., cross-sectional depth imaging). By capturing a plurality of OCT "slices" at different locations along the y-direction, the slices can be combined to recreate a 3D OCT volume. At the same time, SER image data captured while the coordinated oscillations provide scanning in two dimensions provides a two-dimensional SER image in a plane orthogonal to each OCT "slice" (e.g., a surface image).

The SER and OCT image data captured by the SECTR imaging components 109 is digitized by a digitizer 111 and the digitized image data is transmitted to the image processing system 103. The image processing system 103 includes one or more electronic processors 113 and one or more non-transitory computer-readable memories 115. The memory 115 stores instructions that are accessed and executed by the electronic processor 113 to provide the functionality of the image processing system 103. As described in further detail below, the image processing system 103 is configured to apply a trained neural network to the captured SER image data to detect and determine the location of a surgical instrument in the 2D SER image data. In some implementations, the image processing system 103 includes one or more dedicated processors (e.g., a graphics processing unit (GPU)) configured to perform the neural network processing while another electronic processor executes other instructions to provide other functionality of the image processing system 103.

Once the location of the surgical instrument is identified in the 2D plane of the SER image data, data indicative of the determined location of the surgical instrument is transmitted from the image processing system 103 to the waveform generator system 105. A communication port or a separate communication device 117 receives the instrument tracking/position information from the image processing system 103 and provides the instrument position information to an electronic processor 119 of the waveform generator system 105. The waveform generator system 105 also includes a non-transitory computer-readable memory 121 storing data and instructions that are accessed & executed by the electronic processor 119 to provide the functionality of the waveform generator system 105.

The electronic processor 119 of the waveform generator system 105 is configured to generate a waveform to control the oscillations of the galvanometer controllers 107 based on a laser trigger signal 123 and the instrument position information received from the image processing system 103. In particular, in some implementations, the laser trigger 123 defines the base oscillation waveform and the electronic processor 119 is configured to offset the waveform from the laser trigger 123 based on the instrument position information. A digital-to-analog converter 125 converts the control waveform from the electronic processor 119 to an analog signal and applies the analog waveform to the galvanometer controller 107 to control the oscillation of the imaging components 109. In some implementations that includes multiple galvanometer controllers 107 configured to perform oscillations in multiple different directions, the waveform generator system 105 may be configured to provide multiple different control waveforms—one to each galvanometer controller of the plurality of galvanometer controllers 107—with each control waveform thereby controlling an oscillation range in a different direction.

In some implementations, the image processing system 103 and the waveform generator system 105 are provided as separate computing platforms. For example, the image processing system 103 may be implemented on a desktop or laptop computer while the waveform generator system is implemented as a separate stand-alone device. Accordingly, in some implementations, the functionality of the electronic processor 113 and the electronic processor 119 (such as described herein) may be implemented by different electronic processors (as illustrated in FIG. 1) or by the same single electronic processor.

In one specific example implementation, the image capture system 101 is provided as a swept-source laser with 1050 nm and 105 nm bandwidth. The system line-rate is 400 kHz and imaging throughput is 2.3 gigasamples per second. In this example, a state-of-the-art GPU-accelerated convolution neural network (CNN) is implemented by the image processing system 103 and is trained on 900 manually-labeled SER frames for detection of ILM forceps and integrated with custom C++ image acquisition software. In this example, the image processing system 103 is implemented as a desktop computer running Windows 10 on an octo-core Xeon E5 CPU, 64 GB RAM, and a NVIDIA GeForce GTX 1060 GPU with 3 GB of memory. The electronic processor 119 of the waveform generator system 105 is provided as an ARM-based microcontroller board (STM32F4-Discovery, STMicroelectronics) configured to output control waveforms that provide a sawtooth scan pattern with sinusoidal fly-back. An Arduino microcontroller (i.e., communication device 117) was configured to arbitrate communication between the PC (i.e., the image processor system 103) and the ARM board (i.e., the waveform generator system 105) over serial-peripheral interface (SPI). In this specific example, a direct memory access (DMA) controller 127 was also used on the ARM board to store the instrument position information directly to the memory 121 in order to reduce computational load on the electronic processor 119. The control waveform calculated by the electronic processor 119 is sent to a 14-bit digital-to-analog converter 125 (DAC8803, Texas Instruments) over a separate SPI channel and the generated control waveform signals are then output by the DAC 125 to drive the galvanometer scanners (i.e., galvanometer controllers 107).

Figure 2:
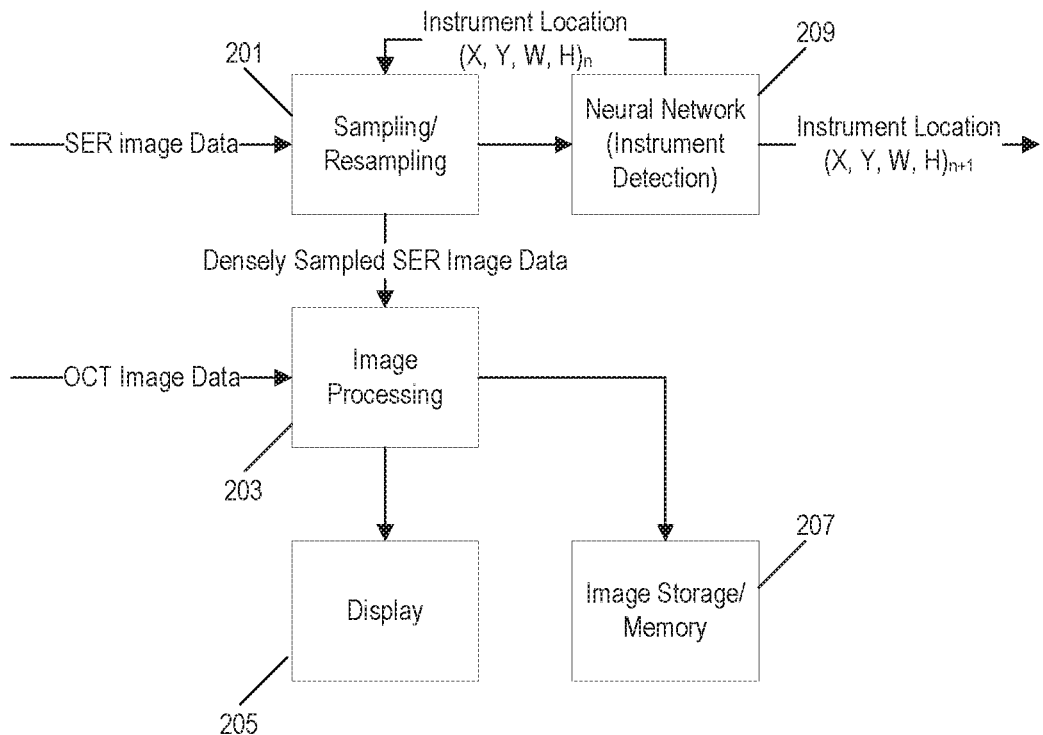
FIG. 2 is a functional block diagram illustrating operations performed by the image processing system of FIG. 1 to capture image data and track the location of the instrument.

FIG. 2 illustrates an example of the functions performed by the image processing system 103 in capturing, displaying, and storing image data while also determining the position of a surgical instrument based on the image data. The image processing system 103 receives the SER image data and OCT image data. In some implementations, the SER image data and the OCT image data are received as digitized streams from the image capture system 101 while incoming data is sampled & stored (step 201) at one or more defined sampling rates. In some such implementations, adaptive sampling may be implemented by using a higher sampling rate (e.g., dense sampling) for image data in scanning locations corresponding to the previously determined position of the instrument and a lower sampling rate (e.g., sparse sampling) for image data at all other locations not corresponding to the position of the instrument. In other implementations, adaptive sampling is performed by adjusting the fast-axis scan speed through the control waveform output to the galvanometer controller 107 to decrease the scan/oscillation speed for dense sampling at locations corresponding to the determined position of the instrument and increasing the scan/oscillation speed for sparse sampling of the periphery. In some implementations where adaptive sampling is provided by varying the scan/oscillation speed, a constant sampling rate can be used.

Image processing 203 is applied to the densely sampled (i.e., relatively high resolution) portion of the SER image data and the OCT image data in order to provide the real-time feedback of the iOCT-guided surgery. In some implementations, the image processing 203 also uses the received OCT "slices" to generate 3D volumetric OCT images. Four-dimensional OCT images can also be provided by generating 3D volumes based on the captured OCT data for each of a plurality of scan sequences over time showing movement of the surgical instrument and surrounding tissue. Processed image data can be shown to a user on a graphical display 205 and/or stored to an image storage/memory 207 for future use or analysis.

Figure 4:
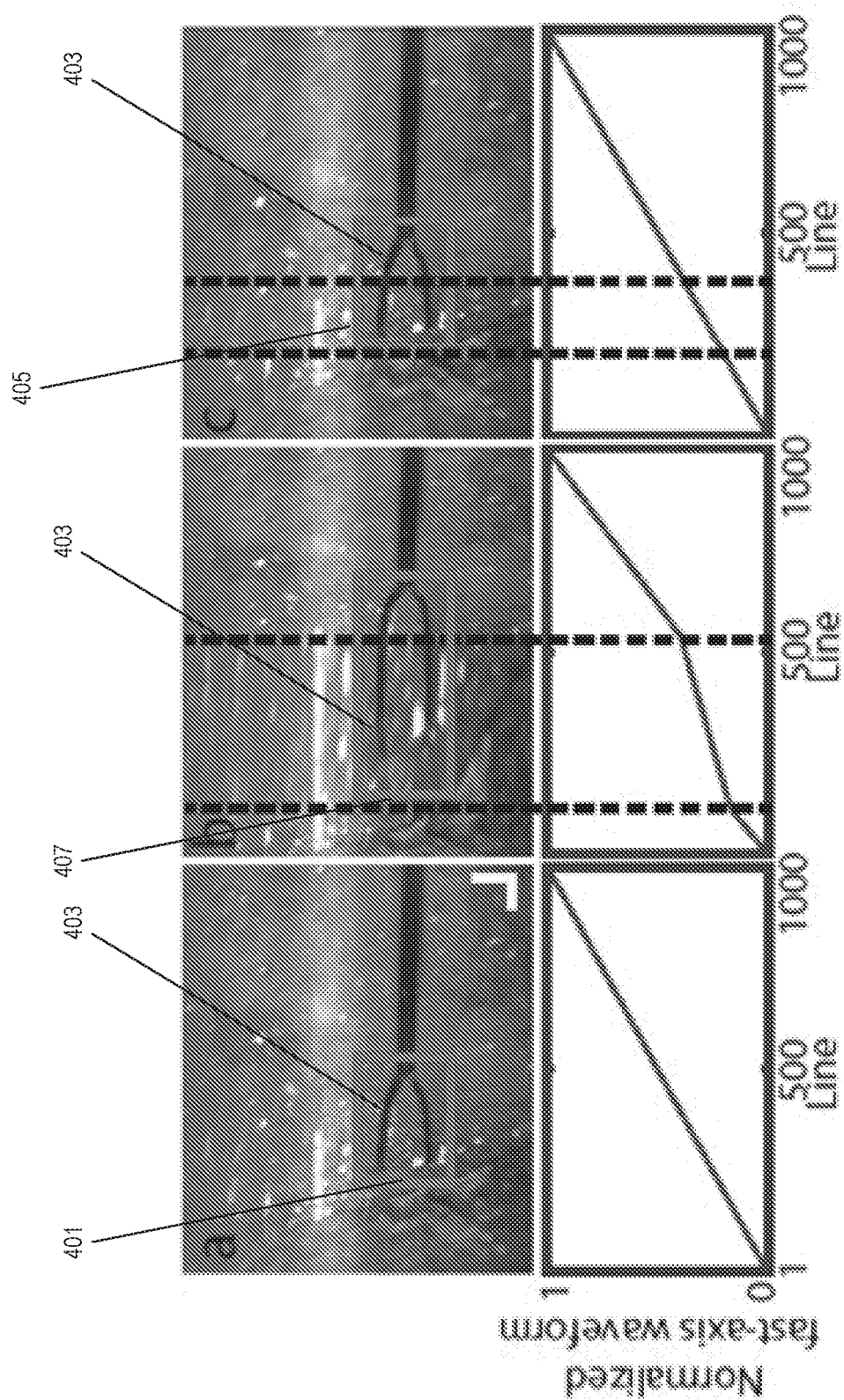
FIG. 4 is a first sequence of SER image frames and corresponding graphs illustrating adaptive sampling adjustments to the scanning waveform based on a determined location of the instrument in the system of FIG. 1.

To determine an updated location of the surgical instrument based on the newly received SER image data, the SER image frame is resampled to provide an image of uniform density including both the densely sampled areas and the sparsely sampled areas. This resampling is described in further detail below with respect to FIG. 4. The resampled SER image is provided as input to a trained neural network 209, which provides as output a determined location of the surgical instrument. In some implementations, the neural network 209 is configured to output the determined location as a two-dimensional "bounding box" positioned around the location of the tip of the surgical instrument in the SER image frame. In the example of FIG. 2, the neural network provides the "bounding box" as output by defining a location of a corner of the bounding box using (X, Y) coordinates and by defining a width and height of the bounding box.

Figure 3:
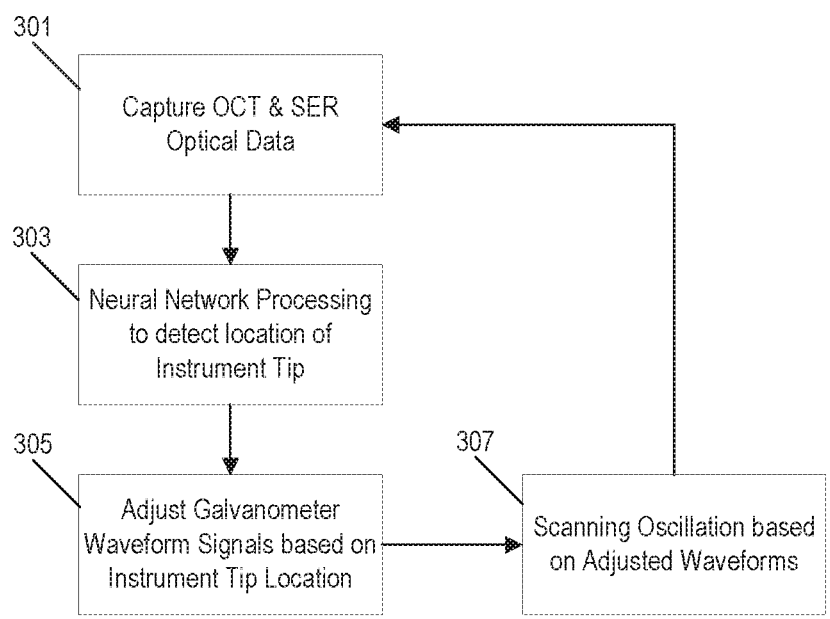
FIG. 3 is a flowchart of a method for automated spatial and temporal adjustments to the image scanning based on a determined location of the instrument in the system of FIG. 1.

FIG. 3 summarizes the operation of the image tracking functionality as described above in reference to the specific examples of FIGS. 1 and 2. OCT and SER image data is captured by the image capture system 101 (step 301). Neural network processing is applied to the SER image frame to detect a location of the instrument tip in the SER image frame (step 303). A control waveform signal is generated based on the determined location of the instrument tip (step 305) and the scanning oscillations of the image capture system are controlled to adjust the field-of-view of the imaging system to account for detected changes in a position of the instrument tip (step 307) as new OCT and SER optical data is captured (step 301).

As discussed above, in some implementations, adaptive sampling is provided by adjusting the oscillation speed of the imaging components (while the sampling rate remains static) when scanning areas corresponding to a determined location of the tip of the surgical instrument. In some such implementations, the captured SER image data is then resampled in order to generate an image of uniform resolution that can be provided as input to the neural network. This is illustrated further in the example of FIG. 4. The first image (labelled "a" and shown in the left column of the top row in FIG. 4) shows an SER image frame and a bounding box 401 around the instrument tip 403. The second image (labelled "b" and shown in the middle column of the first row in FIG. 4) shows a subsequent SER image frame captured based on the determined position of the instrument tip 403 as indicated by the bounding box 401 for the previous frame. When capturing this second image, the fast-axis oscillation speed of the galvanometer controller was slowed in areas corresponding to the determined location of the instrument tip. This is illustrated further by the graphs of the normalized fast-axis waveform provide below each image. In the waveform graph for the first image, the oscillation speed is constant across the entire width of the image area. However, the waveform graph for the second image shows that the oscillation speed is temporarily slowed when scanning over areas corresponding to the determined location of the instrument tip in the previous SER image.

The area between the two dashed lines in the second image (and its corresponding fast-axis waveform graph) indicated areas corresponding to the previously determined location of the instrument tip. In the graph, the change in oscillation speed is indicated by a decreased slope in the waveform. As shown in the second image, the slowed oscillation speed resulted in the acquisition of more data in the area between the dashed lines and causes the resulting image to appear "stretched" in the area corresponding to the determined location of the instrument tip in the first image. Accordingly, before the new SER image frame is provided as input to the neural network, the new SER image frame is resampled based on the determined location of the instrument tip from the previous image (which is known by the image processing system 103) to provide a consistent spatial image resolution and to thereby remove the "stretching" effect. The resampled image is shown as the third image (labelled "c" and shown in the top row of the right column). The image correction achieved by this resampling is confirmed by the graph below the third image indicating a continuous oscillation speed for the effective fast-axis waveform for the resampled third image (i.e. a continuous slope for the corresponding graph).

When the third image is provided as an input to the neural network, the location of the instrument tip 403 is indicated by a new bounding box 405. The dimensions of this same bounding box are illustrated in the original SER image data before the resampling (i.e., in the image in the center column of the top row in FIG. 4) by bounding box 407 to illustrate the difference between the location of the instrument tip in the original captured/sampled SER image data and in the resampled/corrected SER image data.

Figure 5:
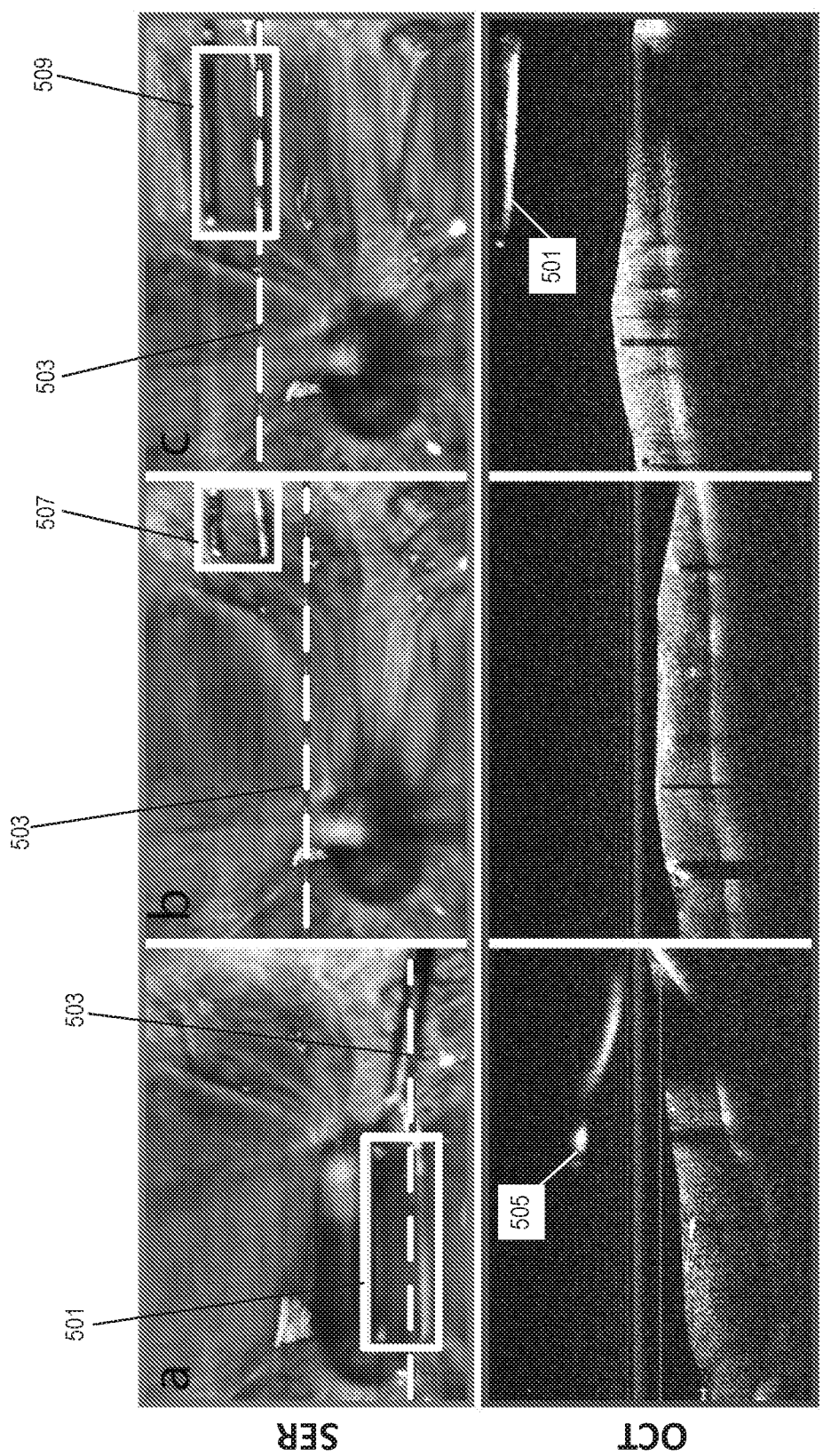
FIG. 5 is a second sequence of SER image frames showing movement of an instrument out of an OCT imaging plane and a corresponding 2D OCT scan frame for each SER image frame illustrating adjustments to a position of an OCT scan plane based on a detected change in the location of the instrument using the system of FIG. 1.

In some implementations, the position of the image capture system 101 itself may remain stationary during a surgical procedure and, as described above, the field of view of the captured image data is adjusted through the control waveform generated & applied to the galvanometer controllers that provide the scanning oscillation. FIG. 5 provides an example of how the OCT field-of-view is adjusted based on a determined position of the instrument tip in the SER image frame. Each column illustrates an SER image frame and a corresponding 2D OCT image "slice" captured at three different sequential times. In the first SER image (top row, left column), the location of the instrument tip is indicated by the bounding box 501. As noted above, the OCT imaging plane is orthogonal to the SER imaging plane. The location of the OCT imaging plane for the first OCT image "slice" (bottom row, left column) is indicated by the dashed line 503 in the first SER image.

As shown in the first SER image, the OCT imaging plane 503 runs through the bounding box 501 defining the location of the instrument tip. Accordingly, the instrument tip 505 is also visible in the first OCT image "slice." In the second SER image (top row, middle column), the instrument tip has been moved relative to the SER imaging plane and it's new position is indicated by the bounding box 507. As shown in the second SER image, the OCT imaging plane 503 does not run through the bounding box 507 and, therefore, the instrument tip 505 is not visible in the second OCT image "slice" (bottom row, middle column) corresponding to the second SER image. However, by the time that the third SER image (top row, right column) is captured, the output waveform has been adjusted to capture the OCT image data in an OCT imaging plane 503 that does run through the bounding box 509. Accordingly, the instrument tip 505 is once again visible in the third OCT image "slice" (bottom row, left column) corresponding to the third SER image.

Figure 6:
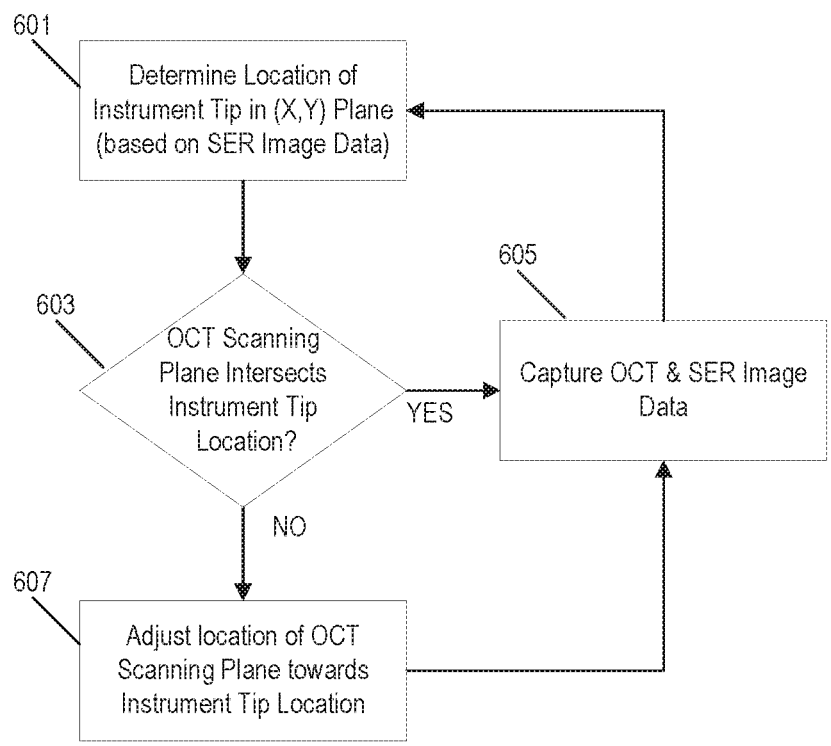
FIG. 6 is a flowchart of a method for adjusting a position of an OCT scan plane based on a determined location of the instrument in the system of FIG. 1.

FIG. 6 illustrates a method for adjusting the location of a 2D OCT imaging plane based on a determined location of an instrument time in a 2D imaging plane that is orthogonal to the OCT imaging plane. First, a location of the instrument tip is determined in the (X, Y) plane based on the SER image data (step 601) (e.g., using the neural network mechanism described above). If the current position of the OCT scanning plane intersects the determined location of the instrument tip (step 603), no adjustment is required and subsequent OCT & SER image data is captured (step 605). However, if the OCT scanning plane does not intersect with the determining location of the instrument tip (e.g., as shown in the second SER image of FIG. 5), then one or more of the control waveforms produced by the waveform generator system 105 is adjusted to move the location of the OCT scanning plane towards the determined location of the instrument tip (step 607) before subsequent OCT & SER image data is captured.

As discussed above, the adaptive sampling mechanism is used to provide higher resolution SER imaging in imaging areas corresponding to a determined location of the instrument tip. In some implementations, adaptive sampling is also used to more densely sample the OCT image data in those same areas. However, in other implementations, SER image data is collected at different sampling resolutions based on the determined location of the instrument tip while OCT data is only collected in areas corresponding to the determined location of the instrument tip. This allows for 3D volumetric reconstruction of the instrument tip and the nearby biological tissue from the captured OCT data while reducing computational load by not capturing or processing OCT data from other areas further away from the instrument tip.

Figure 7:
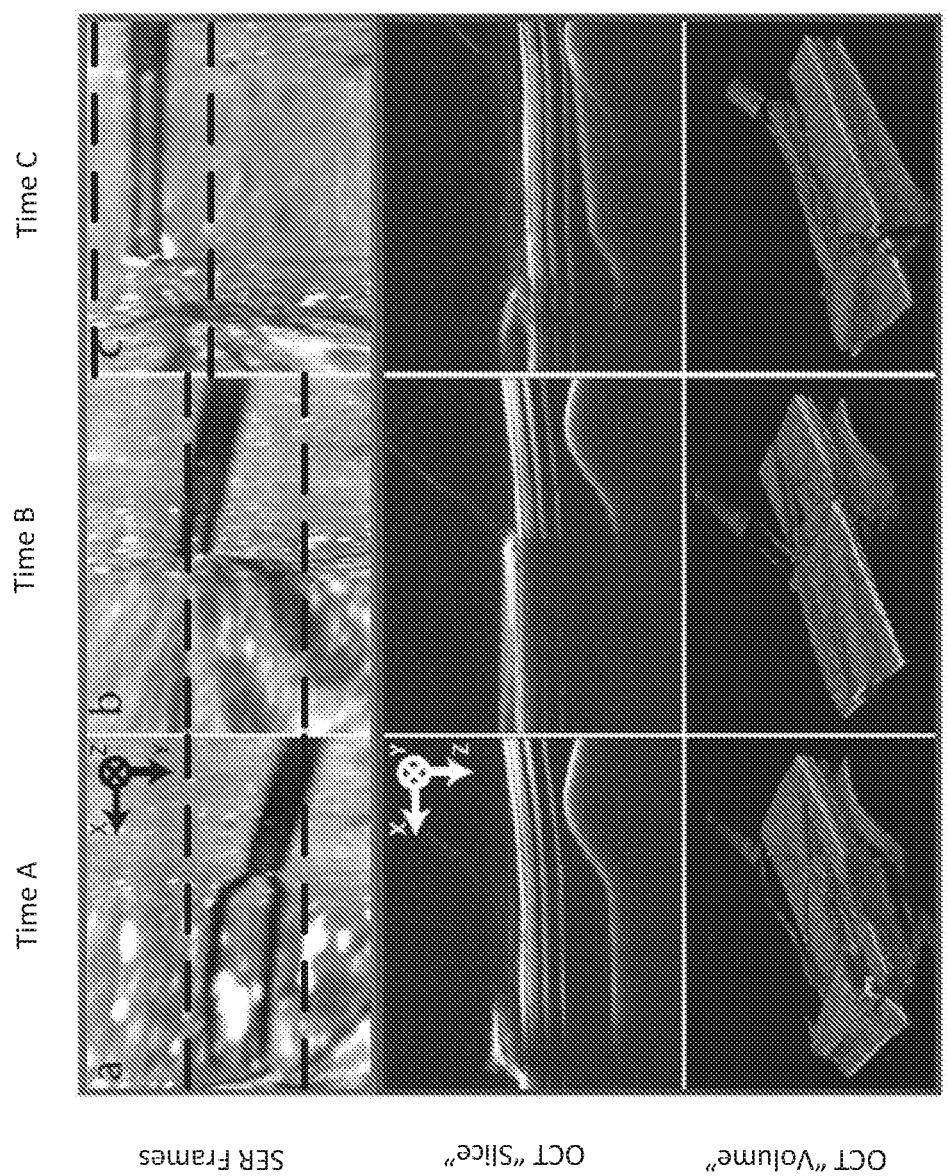
FIG. 7 is a third sequence of SER image frames showing movement of an instrument relative to a 3D OCT field-of-view volume and a corresponding 2D OCT scan frame & 3D OCT reconstructed volume for each SER image frame illustrating an automated adjustment to the 3D OCT field-of-view based on a detected change in the location of the instrument using the system of FIG. 1.

FIG. 7 illustrates an example of how the system of FIG. 1 may adjust the OCT field-of-view based on the determined location of the instrument tip in the SER image frames. Each column includes an SER image frame, a single 2D OCT "slice," and a 3D OCT "volume" reconstruction from image data captured at three different sequential times (time A, time B, and time C). As discussed above, the OCT "slice" data is captured in an OCT imaging plane that is orthogonal to the imaging plane of the SER image. Each OCT "slice" is captured by scanning along the x-axis (i.e., the fast-axis) and advancing the scan in the Y-direction at a slower speed to capture additional OCT "slices." The OCT slices are then combined to generate the OCT volume. In each SER image frame, a pair of dashed lines indicates the boundaries in the Y-scanning direction of the determined location of the instrument tip. In this example, only OCT slice data captured by x-direction scans performed within this y-direction range are used by the system to construct the 3D OCT "volume."

As shown in the SER image frame for "Time A," the instrument tip is located entirely within the y-direction range defined by the dashed lines (i.e., the y-direction range corresponding to the determined location of the instrument tip in the previous SER image frame). Accordingly, the 3D volume reconstructed from the OCT image slices includes the entire instrument tip, which appears centered in the y-direction of the field-of-view of the 3D OCT data. However, at "Time B," the instrument tip has been moved in the y-direction and is approaching the edge of the y-direction range corresponding to the previously determined location of the instrument tip. Accordingly, the instrument tip is no longer centered in the 3D volume reconstructed from the captured OCT data at "Time B." By "Time C," the neural-network processing is able to correctly identify the new position of the instrument tip in the y-direction and has defined a new y-direction range corresponding to the new location of the instrument tip. By adjusting the oscillation waveforms and controlling the image sampling to only use OCT slice data captured within the new y-direction range corresponding to the new detected locating of the instrument tip, the 3D volume reconstructed from the OCT data for "Time C" again presents the instrument tip centered in the y-direction.

The specific methods and systems described above provide only a few examples of implementations of the invention. Other configurations and implementations of the methods, systems, and functionality described above are possible. For example, although the example described above utilize a SECTR imaging platform in which enface SER images are captured and analyze to provide the automated instrument tracking functionality for guiding the OCT imaging, in other implementations, other types of forward-facing, enface imaging platforms and/or other depth-imaging techniques may be used. For example, in some implementations, another type of forward-facing, enface imaging platform (including, for example, other camera-based systems) may be used to capture the enface imagery as discussed above, which is then analyzed by the image processing system to identify a location of the instrument in order to guide OCT imaging. Similarly, other 3D or depth-based imaging system (including, for example, ultra-sound imaging and laser-based surface scanning) may be used to generate 3D imagery including the instrument tip based on a determined location of the tip from the enface imaging platform.

Additionally, although the example above discuss generating a waveform based on the determined position of the instrument tip and providing the generated waveform to one or more galvanometer controllers in order to control the speed, direction, and position/range of the scanning oscillations of the imaging system components, in some implementations, other movement stages are used to control the movement/positioning of the imaging components based on the determined location of the instrument. In some such implementations, the "waveform generator system" described in the examples above may be replaced with another electronic controller configured to generate an output signal that is appropriate to control the speed, direction, and position/range of the movement stage that is utilized for movement of the imaging components.

Finally, although the examples above specifically discuss a system configured to determine a location of a tip of an instrument (i.e., a forceps instrument), some implementations maybe configured to detect the location of other types of instruments and/or other portions of the instrument. Some implementations may be configured to identify only a single type of medical instrument while, in other implementations, the image processing system may be configured to detect the location of multiple different types of medical instruments. In some cases, a user input is provided to instruct the image processing system (e.g., the neural-network) which type of instrument to track in the captured image data. In other implementations, the neural-network may be configured to generate appropriate bounding boxes for any of several different types of instruments without a specific identification of the tool from a user.

Accordingly, this invention provides, among other things, systems and methods for automated instrument tracking and adaptive-sampling for intraoperative OCT. Various features and advantages of the invention are set forth in the following claims.

What is claimed is:

1. An image-based guidance system comprising:
a first imaging system configured to capture en face image data in a first imaging plane;
a second imaging system configured to capture depth image data in a second imaging plane, the second imaging plane being orthogonal to the first imaging plane;
a movement stage configured to provide a scanning movement of the second imaging system; and
an electronic controller configured to:
receive an en face image frame based on the en face image data captured by the first imaging system,
analyze the en face image frame to determine a location of an instrument in the first imaging plane,
generate a control signal for the movement stage based on the determined location of the instrument, wherein the control signal is generated to cause the movement stage to position the second imaging system to capture the depth image data at the determined location of the instrument, and
transmit the control signal to the movement stage,
wherein the electronic controller is further configured to receive the depth image data from the second imaging system while scanning movement of the second imaging system is controlled based on the generated control signal,
wherein the electronic controller is further configured to generate the control signal by generating a control signal configured to decrease the speed of scanning movement in areas corresponding to the determined location of the instrument in the first imaging plane to provide an increased sampling density in the areas corresponding to the determined location of the instrument.

2. The system of claim 1, wherein the electronic controller is configured to analyze the en face image frame to determine a location of an instrument in the first imaging plane by providing the en face image frame as input to a neural network trained to produce as an output a bounding box defining the location of the instrument in the first imaging plane.

3. The system of claim 1, wherein the first imaging system includes a spectrally-encoded reflectometry (SER) imaging system and the second imaging system includes an OCT imaging system.

4. The system of claim 3, wherein the movement stage includes
a first galvanometer coupled to the at least one imaging component of the OCT imaging system and configured to provide scanning oscillations of the OCT imaging system in a first scanning direction based on a first control waveform, and
a second galvanometer coupled to the at least one imaging component of the OCT imaging system and configured to provide scanning oscillations of the OCT imaging system in a second scanning direction based on a second control waveform, wherein the second scanning direction is orthogonal to the first scanning direction in the first imaging plane,
wherein the electronic controller is configured to transmit the control signal to the movement stage by transmitting the first control waveform to the first galvanometer and transmitting the second control waveform to the second galvanometer.

5. The system of claim 1, wherein the movement stage is configured to control co-registered scanning movement of the first imaging system and the second imaging system based on the generated control signal,
wherein the electronic controller is further configured to receive additional en face image data while scanning movement of the first imaging system and the second imaging system is controlled based on the generated control signal, and
wherein the generated control signal causes an increased sampling density in the additional en face image data captured by the en face imaging system when scanning in areas corresponding to the determined location of the instrument.

6. The system of claim 5, wherein the electronic controller is further configured to:
resample the additional en face image data to generate an additional en face image frame with a uniform spatial resolution,
analyze the additional en face image frame to determine an updated location of the instrument in the en face image frame, and
adjust the generated control signal based on the updated location of the instrument.

7. A method for image-based guidance using automated instrument tracking, the method comprising:
receiving, by an electronic controller, an en face image frame based on en face image data captured by a first imaging system in a first imaging plane;
analyzing the en face image frame to determine a location of an instrument in the first imaging plane;
generating a control signal for a movement stage based on the determined location of the instrument, wherein the movement stage is configured to provide scanning movement of a second imaging system, the second imaging system configured to capture depth image data in a second imaging plane during the scanning movement, the second imaging plane being orthogonal to the first imaging plane; and
transmit the control signal to the movement stage; and
receiving the depth image data from the second imaging system while the scanning movement of the second imaging system is controlled based on the generated control signal, wherein generating the control signal includes generating a control signal configured to decrease the speed of scanning movement in areas corresponding to the determined location of the instrument in the first imaging plane to provide an increased sampling density in the depth image data the areas corresponding to the determined location of the instrument, and wherein the movement stage is configured to control co-registered scanning movement of the first imaging system and the second imaging system based on the generated control signal, the method further comprising receiving additional en face image data while scanning movement of the first imaging system and the second imaging system is controlled based on the generated control signal, wherein the generated control signal causes an increased sampling density in the additional en face image data captured by the en face imaging system when scanning in the areas corresponding to the determined location of the instrument.

8. The method of claim 7, wherein analyzing the en face image frame to determine the location of the instrument in the first imaging plane includes providing the en face image frame as input to a neural network trained to produce as an output a bounding box defining the location of the instrument in the first imaging plane.

9. The method of claim 7, wherein receiving the en face image frame based on the en face image data captured by the first imaging system includes receiving a spectrally-encoded reflectometry (SER) image frame based on SER image data captured by an SER imaging system, and further comprising receiving OCT image data from the second imaging system during the scanning movement of the second imaging system, wherein the second imaging system is an OCT imaging system.

10. The method of claim 9, wherein the movement stage includes a first galvanometer configured to provide scanning oscillations of the OCT imaging system in a first scanning direction based on a first control waveform, and a second galvanometer configured to provide scanning oscillations of the OCT imaging system in a second scanning direction based on a second control waveform, wherein the second scanning direction is orthogonal to the first scanning direction in the first imaging plane, wherein transmitting the control signal to the movement stage includes transmitting the first control waveform to the first galvanometer and transmitting the second control waveform to the second galvanometer.

11. The method of claim 7, further comprising:
resampling the additional en face image data to generate an additional en face image frame with a uniform spatial resolution;
analyzing the additional en face image frame to determine an updated location of the instrument in the first imaging plane; and
adjusting the generated control signal based on the updated location of the instrument.

12. An image-based guidance system comprising:
an OCT imaging system configured to captured depth image data;
a first galvanometer coupled to at least one imaging component of the OCT imaging system to provide scanning oscillations of the OCT imaging system in a first scanning direction;
a second galvanometer coupled to the at least one imaging component of the OCT imaging system to provide scanning oscillations of the OCT imaging system in a second scanning direction, the second scanning direction being orthogonal to the first scanning direction in a first imaging plane;
an en face imaging system configured to capture en face image data in the first imaging plane, wherein the en face imaging system is positionally co-registered with the OCT imaging system, and wherein at least one imaging component of the en face imaging system is coupled to the first galvanometer and the second galvanometer to provide scanning oscillations of the en face imaging system in the first scanning direction and the second scanning direction;
an electronic controller configured to:
receive an en face image frame based on the en face image data captured by the en face imaging system,
apply a neural network configured to receive the en face image frame as an input and to produce as output a bounding box defining a determined location of an instrument tip in the first imaging plane,
generate a first control waveform for the first galvanometer and a second control waveform for the second galvanometer, wherein the first control waveform is generated based on the determined location of the instrument tip in the first scanning direction, and wherein the second control waveform is generated based on the determined location of the instrument tip in the second scanning direction,
transmit the first control waveform to the first galvanometer and the second control waveform to the second galvanometer to control scanning oscillations of the OCT imaging system, and
receive OCT image data from the OCT imaging system while the scanning oscillations of the OCT imaging system are controlled based on the first control waveform and the second control waveform,
wherein the electronic controller is configured to generate the first control waveform by defining a waveform configured to decrease the speed of scanning oscillations of the OCT imaging system in the first scanning direction when scanning in areas corresponding to the determined location of the instrument tip in the first imaging plane to provide an increased image sampling density in the areas corresponding to the determined location of the instrument tip.

13. The system of claim 12, wherein the electronic controller is further configured to receive additional en face image data while the scanning oscillations of the OCT imaging system is controlled based on the first control waveform and the second control waveform, and wherein the first control waveform causes an increased sampling density in the additional en face image data captured by the en face imaging system when scanning in areas corresponding to the determined location of the instrument tip.

14. The system of claim 13, wherein the electronic controller is further configured to resample the additional en face image data to generate an additional en face image frame with a uniform spatial resolution,
provide the additional en face image frame as input to the neural network to determine an updated location of the instrument tip, and
adjust the first control waveform and the second control waveform based on the updated location of the instrument tip.

15. The system of claim 12, wherein the en face imaging system is a spectrally-encoded reflectometry (SER) imaging system, and wherein the en face image data is SER image data.

\* \* \* \* \*